United States Patent [19]

Vyas

[11] Patent Number: 4,596,792
[45] Date of Patent: Jun. 24, 1986

[54] SAFE VACCINE FOR HEPATITIS CONTAINING POLYMERIZED SERUM ALBUMIN

[75] Inventor: Girish N. Vyas, Orinda, Calif.

[73] Assignee: The Regents of the University of California, Berkeley, Calif.

[21] Appl. No.: 595,636

[22] Filed: Mar. 30, 1984

Related U.S. Application Data

[63] Continuation of Ser. No. 299,452, Sep. 4, 1981, abandoned.

[51] Int. Cl.$^4$ .............................................. A61K 37/02
[52] U.S. Cl. ......................................... 514/21; 514/2; 424/85; 424/86; 424/89
[58] Field of Search ............... 424/85, 86, 177; 514/2, 514/21

[56] References Cited

U.S. PATENT DOCUMENTS 4,046,871 9/1977 Reckel .................................. 424/101

OTHER PUBLICATIONS

Hansson et al.—Infection and Immunity, vol. 26, No. 1, pp. 125-130.
Shenvi et al.—Fed. Proc., vol. 38, (3 part II) (1979), p. 1159.
O'Neill—J. of Med. Vir., vol. 4 (1979), pp. 177-185.
O'Neill—Chem. Abst. vol. 92 (1980), pp. 20449f.
Milich et al.—Chem. Abst. vol. 95 (1981), p. 201,845q.
Milich et al.—Chem. Abst. vol. 95 (1981), p. 201846r.
Thung et al. (1981), Infection and Immunity, vol. 32, No. 3, 1292-1294.
Neurath et al. (1974), PNAS USA vol. 71, No. 7, 2663-2667.
Ionescu-Matiu et al. (1980), Journal of Med. Virol. 6:175-178.
Tiollais et al. (1981), Science, vol. 213, 406-411.
Onica et al. (1980), Mol. Immunol. vol. 17, 783-789.
Lenkei et al. (1977), Journal of Med. Virol. 1, 29-34.
Onica et al. (1978), Immunochemistry, vol. 15, 941-944.
Lenkei and Ghettie (1977), Journal of Immunol. Methods, 16, 23-30.
Imai et al. (1979), Gastroenterology, vol. 76, 242-247.
Milich et al. (1980), Gastroenterology, vol. 79, 1116.
Milich et al., (1981), Gastroenterology, vol. 81, 218-225.
Onica et al., Chem. Abstract (1979), 90:459, #202079b.
Milich et al., Chem. Abstract (1981) 95:499, #201845r.

Primary Examiner—Sam Rosen
Attorney, Agent, or Firm—Bertram I. Rowland

[57] ABSTRACT

Methods and compositions are provided for an inexpensive safe vaccine for hepatitis infection. Immunogenic polymerized human albumin free of other hepatitis related immunogens is employed in a physiologically acceptable carrier as a vaccine for protection against hepatitis.

6 Claims, No Drawings

SAFE VACCINE FOR HEPATITIS CONTAINING POLYMERIZED SERUM ALBUMIN

CROSS-REFERENCE TO RELATED APPLICATIONS

This is a continuation of application Ser. No. 299,452, filed Sept. 4, 1981 now abandoned.

BACKGROUND OF THE INVENTION

1. Field of the Invention

Hepatitis is a viral disease which can exist in both infectious and non-infectious form. It is of particular concern because of its transmission through blood transfusions. It is known that there are many carriers of the virus which are not subject to the symptoms of the disease. Nevertheless, these people are able to transmit the disease to others who are susceptible to infection, particularly through blood transfusions, where the blood is not carefully monitored.

Because of the widespread character of hepatitis, it would be desirable to be able to vaccinate people for the disease. For the most part, vaccines have relied upon the protein coat of the virus, which is only difficultly attainable and must be carefully purified to avoid any inclusion of the viral chromosome. Because of the expensive nature of the isolation and purification of the protein coat, an inexpensive vaccine has not been available which could be used, particularly in those areas which are unable to afford the high cost of the presently available vaccines.

2. Description of the Prior Art

Human serum albumin and the hepatitis B surface antigen are associated with the viral coat protein of the hepatitis B virus. Neurath et al. (1974) PNAS USA 71:2663; Ionescu-Matiu et al. (1980) J. Med. Virol. 6:175; Tiollais et al. (1981) Science 213:406. Thus, common occurrence of albumin molecules in the coat protein of viruses replicating in the liver is naturally expected. In vitro aging or heat or glutaraldehyde polymerization of albumin results in a product which elicits antibodies in immunized animals. Onica et al. (1980) Mol. Immunol. 17, 783. Antibodies to polymerized albumin have also been encountered in the sera of patients with acute or chronic liver disease. Lenkei et al. (1977) J. Med. Virol. 1, 29. Physiological and pathological production of antibodies to polymerized human albumin (PHALB) have been studied by Onica and Lenkei (Onica et al (1978) Immunochemistry 15, 941; Lenkei and Ghetie (1977) J. Immunol. Methods 16, 23 and Imai et al. (1979) Gastroenterology 76, 242. The interaction of PHALB with Clq and the relationship of serologic reactivity with PHALB in sera from patients with and without liver disease have been reported be Milich et al. (1980) Gastroenterology 79, 1116, and Milich et al (1981) Gastroenterology 81, 218.

SUMMARY OF THE INVENTION

A safe inexpensive vaccine is provided by employing polymerized human albumin in a physiologically acceptable carrier as a vaccine for hepatitis in the absence of other hepatitis virus derived immunogens. By polymerizing human albumin to provide at least a hexamer, an active immunogen is produced which upon injection produces an immunogenic response to PHALB, but not to monomeric albumin, affording the host protection from hepatitis.

DESCRIPTION OF THE SPECIFIC EMBODIMENTS

Polymerized human serum albumin (PHALB) is prepared and employed in a physiologically acceptable carrier as a vaccine for hepatitis virus. The polymerized albumin composition is desirably on the average at least a hexamer, preferably about an octamer and should generally be less than about a dodecamer, preferably less than about a decamer (6–12; 7–10), wherein 90 or greater weight percent is of the same degree of polymerization, more preferably having the average composition of an octamer. The polymerized human albumin can be formed in any conventional way, by aging, using heat or light, by chemical cross linking, for example, with aldehydes e.g. formaldehyde, dialdehydes, e.g. glutaraldehyde, or other physiologically acceptable tanning agents. Conditions can be chosen so as to optimize the formation of the desired degree of polymerization, followed by purification, if desired. Sedimentation or centrifugation may be employed for large scale separation by molecular weight, employing isopycnic banding, gradient density chromatography centrifugation, or molecular seiving by gel chromatography in large columns. The polymerized human albumin may then be chemically or thermally aggregated using physiologically acceptable multivalent cations or heat.

While the polymerized albumin has been indicated for humans, polymerized albumin allogeneic for any species can be used for the mammalian species to provide an inexpensive vaccine against hepatitis. Therefore, for domestic animals or other mammals which may be subject to hepatitis infection, the subject invention can be used as a vaccine.

The manner of application may be varied widely. Any of the conventional methods for administration of a dead vaccine are applicable. These include oral application on a solid physiologically acceptable base or in a physiologically acceptable dispersion, parenterally, by injection or the like. The dosage of the vaccine will depend on the route of administration and will vary according to the size of the host. Because the vaccine has few if any side effects, relatively large dosages may be used without injury to the host. Normally, the amount of the vaccine will be from about 1 μg to 20.0 mg per kilogram of host, more usually from about 5 μg to 2.0 mg given subcutaneously or intramuscularly after mixing with an appropriate carrier or an adjuvant to enhance immunization with the vaccine.

Various methods of achieving adjuvant effect for the vaccine includes use of agents such as aluminium hydroxide or phosphate (alum), commonly used as 0.05 to 0.1 percent solution in phosphate buffered saline, admixture with synthetic polymers of sugars (Carbopol) used as 0.25 percent solution, aggregation of the protein in the vaccine by heat treatment with temperatures ranging between 70° to 101° C. for 30 to 2 minute periods respectively, aggregation by reacting with pepsin treated (Fab) antibodies to albumin, mixture with bacterial cells such as *C. parvum* or endotoxins or lipopolysaccharide components of gram-negative bacteria, emulsion in physiologically acceptable oil vehicles such as mannide mono-oleate (Aracel A) or emulsion with 20 percent solution of a perfluorocarbon (Fluosol-DA) used as a blood substitute. More novel methods of adjuvanticity would include bacterial toxins against which the host has been preimmunized, for example by coupling 5 moles of the vaccine per mole of tetanus toxoid or diptheria toxoid, the compound vaccine could elicit enhanced immune response to PHALB. The amount of the adjuvant will vary widely depending upon the nature of the adjuvant, generally varying from 0.1 to 100 times the weight of the immnogen, more usually from 1 to 10 times.

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1–5 years, usually three years, will be desirable to maintain protective levels of the antibodies. The course of the immunization may be followed by assays for antibodies for PHALB. The assays may be performed by labelling PHALB with conventional labels, such as radionuclides, enzymes, flourescers, and the like. These techniques are well known and may be found in a wide variety of patents, such as U.S. Pat. Nos. 3,791,932, 4,174,384, and 3,949,064, as illustrative of these types of assays. The types of assays may be divided between homogeneous, which do not involve a separation step, and heterogeneous, which do involve a separation step.

Radioimmunoassays are illustrative of the heterogeneous assays. A radioimmunoassay could be performed by binding PHALB to a surface, either a particle or the surface of a container, adding the serum sample to the bound PHALB, and allowing the mixture to incubate for sufficient time for any antibody to PHALB to react with the bound PHALB. One would then add radionuclide-labelled PHALB to the container, incubate for a period of time sufficient for the labelled PHALB to bind any antibody bound to the surface, wash, and then measure the radioactivity bound to the surface. Alternative protocols may also be employed.

In a homogeneous assay, PHALB could be substituted with fluorescer molecules, the labelled PHALB combined with the sample, followed by addition of antibodies to the fluorescer. Depending upon the choice of the fluorescer, binding of the antibody to the fluorescer could result in an increase or decrease in fluorescence. The binding of antibodies to the PHALB will inhibit binding of antibodies to the fluorescer, so that by measuring the fluoresence of the assay medium in comparison with an assay medium having known amounts of antibodies to PHALB, the presence of antibodies to PHALB in the sample could be determined. The particular manner in which the presence of the antibodies to the PHALB in a serum sample is determined is not a significant aspect of this invention.

The following examples are offered by way of illustration and not by way of limitation.

EXPERIMENTAL

To prepare cross-linked PHALB, 120 mg of crystalline human serum albumin (HSA) is dissolved in 3.6 ml of 0.1M phosphate buffer (pH 6.8). Polymerization is accomplished by the addition of 0.4 ml of a 2.5% solution of glutaraldehyde solution in 0.1M phosphate buffer (pH 6.8). After two hours at room temperature, the reaction mixture is dialyzed against 3×500 ml PBS, changed at 3, 6 and 18 hour intervals. The PHALB is then treated with 0.1% sodium borohydride to stabilize the polymer and neutralize unreacted aldehyde groups and then chromatographed through Sephacryl S-300 gel column in PBS. The first major peak is separated and determined to have an average molecular weight of 500,000 daltons.

For the performance of radioimmunoassay, HSA is prelabelled with $^{125}I$ using the chloramine-T or the Hunter-Bolten reagent and then subjected to the above polymerization procedure to obtain $^{125}I$-PHALB probe. Polystyrene beads of 0.5 cm diameter are first coated with a 0.5 mg/ml solution of PHALB in PBS. The PHALB-coated beads are washed with PBS containing 0.2% between 20 and 0.5% BSA (pH 6.4) and air dried. Test sera are serially diluted with PBS and 2.5% BSA (pH 7.2) for titration and to each dilution a PHALB-coated bead is added, incubated for 2 hours at 37° C. and then the beads are washed four times with deionized water. Then each bead is reacted with $^{125}I$-labelled PHALB probe, incubated for 4 hours at 37° C., washed 4X and the radioactivity bound to the bead is counted in a gamma counter. The highest dilution of the serum sample giving counts of more than 2.1 times the negative control is considered positive and the end-point of titration. The negative control beads are coated with polymerized transferrin.

Several human sera from patients with acute hepatitis A, sera from convalescent hepatitis B and sera from chronic nonA/nonB hepatitis reveal the presence of antibodies to PHALB in the gamma globulin fraction. The serologic specificity of the antibodies is established by neutralization reactions using 4 units of limiting antibodies. Both 0.1 μg of PHALB and purified 3.0 μg of hepatitis virus envelope protein neutralize the antibodies, whereas up to 1000 μg of HSA and other plasma proteins fail to inhibit the human antibodies to PHALB. Thus, it is apparent that purified envelope protein of HBV and PHALB share the serologic determinant and indicate that antibodies to PHALB would provide an effective protection against infection by various hepatotropic viruses including the hepatitis B virus.

For preparation of the vaccine, 6.0 mg of PHALB is mixed with 20 mg of mannitol per ml of PBS and heated at 60° C. for 11 hours, followed by heating at 101° C. for 1–2 minutes. The heat-treated PHALB is mixed with equal volume of 0.1% aluminium hydroxide and tested for toxicity and pyrogenicity. The PHALB may then be used as a vaccine for immunization and formulated in the conventional ways. The mineral ion (aluminium) is required for induction of primary immune response, however, because it forms prolonged granuloma at the site of immunization, for the booster the heat-treated PHALB alone, without the adjuvanticity of alum, may be used for secondary immunization.

Effective immunization can be monitored by serologic tests of host serum for antibodies to PHALB. The primary immune response of IgM-type is distinguished from the IgG-type secondary immune response by treatment of the test serum with 0.1M 2-mercaptoethanol. The secondary immune response to PHALB is long lasting and protective against infection with hepatotropic viruses.

In accordance with the subject invention, an inexpensive safe vaccine is provided which can be repeatedly administered to mammalian hosts to provide for a rapid immune response in the event of hepatitis infection by any of the hepatotrophic viruses. Human serum albumin can be readily obtained in pure form and then polymerized to physiological compositions. Thus, populations which cannot afford vaccines prepared by more expensive techniques can have protection from hepatitis.

Although the foregoing invention has been described in some detail by way of illustration and example for purposes of clarity of understanding, it will be obvious that certain changes and modifications may be practiced within the scope of the appended claims.

What is claimed is:

1. A method for protecting a host susceptible to hepatitis infection which comprises:

administering to said host an effective amount of a vaccine consisting essentially of polymerised serum albumin as the immunogen to elicit an immunogenic response in a physiologically acceptable carrier to said host, said polymerized serum albumin having from six to twelve serum albumin units, and being free of any other portions of hepatotropic viruses.

2. A method according to claim 1, wherein said administering is done at least twice to the same host.

3. A method according to claims 1 or 2, wherein said polymerized serum albumin is on the average an octamer.

4. A method according to any of claims 1 or 2, wherein said polymerized serum albumin is thermally or chemically aggregated.

5. A vaccine useful for vaccination for a mammalian host against hepatitis which comprises polymerized serum albumin in combination with an immunogenic adjuvant, wherein said polymerized serum albumin has about six to twelve units, is free of other proteins or genetic material derived from hepatotropic viruses, and is in an amount sufficient to elicit an immunogenic response.

6. A vaccine according to claim 5, wherein said polymerized serum albumin is thermally or chemically aggregated.

* * * * *